United States Patent [19]

Lau

[11] 4,370,501

[45] Jan. 25, 1983

[54] SYNTHESIS OF BIS(AMINOPHENYL) COMPOUNDS

[75] Inventor: Kreisler S. Y. Lau, Alhambra, Calif.

[73] Assignee: Hughes Aircraft Company, Culver City, Calif.

[21] Appl. No.: 308,324

[22] Filed: Oct. 5, 1981

[51] Int. Cl.³ .............................................. C07C 87/50
[52] U.S. Cl. .................................. 564/330; 564/413; 564/430; 564/328
[58] Field of Search ................ 564/328, 330, 413, 430

[56] References Cited

U.S. PATENT DOCUMENTS 3,418,371 12/1968 Krimm et al. ................... 564/330 X
4,177,211 12/1979 Sun ..................................... 564/330

Primary Examiner—Robert V. Hines
Attorney, Agent, or Firm—B. T. Hogan, Jr.; W. H. MacAllister

[57] ABSTRACT

A simplified process for converting bis-phenols to dianilines is disclosed. Selected catalytic complexes are used to cause a nucleophilic displacement reaction between a bis-phenol and a quinazoline to occur thereby yielding a bis-quinazoline that may be subsequently converted into a bis-quinazolinone and hydrolyzed to form the desired dianiline.

8 Claims, No Drawings

SYNTHESIS OF BIS(AMINOPHENYL) COMPOUNDS

The Government has rights in this invention pursuant to Contract No. F33615-78-C-5197 awarded by the Department of the Air Force.

TECHNICAL FIELD

This invention relates, generally, to the synthesis of bis(aminophenyl) compounds and more particularly to the synthesis of 2,2-bis-(4-aminophenyl)hexafluoropropane.

BACKGROUND OF THE INVENTION

1. Field of the Invention

This invention is an aromatic diamine synthesis process. Aromatic diamines are used as intermediates in the synthesis of polyimide oligomers and polymers. The process is particularly useful for the synthesis of 2,2-bis(4-aminophenyl)hexafluoropropane which contains a hexafluoroisopropylidine (6F) group that is known to impart good processability, good thermal stability and good electrical insulation characteristics to the end product polyimide resins. Furthermore, the isolation of UV-vis chromopores by the 6F group allows the end product polyimides to appear colorless.

2. Description of the Prior Art

The chemical conversion of phenols to anilines is an inherently difficult task (see R. A. Scherrer et al. Journal of Organic Chemistry, Vol. 37, pg. 1681 (1972)) that is rendered more difficult when bis-phenols having inductively electron-withdrawing substituents are used as starting materials.

In particular, the chemical conversion of 2,2-bis(4-hydroxyphenyl)hexafluoropropane to other compounds is very difficult because the hydroxy functional groups on a molecule having the 6F groups are resistant to direct chemical modification. However, 2,2-bis-(aminophenyl)hexafluoropropane has been prepared, in low yield, from 2,2-bis(4-hydroxyphenyl)hexafluoropropane that is commercially available under the trade name "Bisphenol AF" from DuPont Chemical Company of Willmington, Del. by K. Paciorek of Ultra Systems Inc. The preparation of 2,2-bis(4-aminophenyl)hexafluoropropane by Dr. Paciorek is described in NASA Report CR-159403 prepared by Ultra Systems Inc. of Irvine, Calif. (Ultra Systems Inc. Report No. SN 8,320-F). The process disclosed in NASA Report CR-159403 is unacceptable for practical use in that it involves strongly corrosive reagents and complex procedures which produce yields of less than 7%. Thus, there is still a need for a simple and efficient process for converting commercially available Bisphenol-AF, and other bis-phenol compounds, to dianiline compounds and there is a need for a simple and efficient process for the conversion of Bisphenol-AF to a dianiline compound having a 6F group between the two phenyl rings.

SUMMARY OF THE INVENTION

The general purpose of this invention is to provide an efficient and simple process for the synthesis of dianilines in general and for the synthesis of 2,2-bis(4-aminophenyl)hexafluoropropane in particular. In accomplishing this purpose, while avoiding the disadvantages of the prior art, and at the same time retaining the advantanges of said art, we have provided an improved process for synthesizing 2,2-bis(4-aminophenyl)hexafluoropropane from Bisphenol-AF is good yields in an efficient manner. The process of this invention involves a nucleophilic displacement reaction, between a bisphenol and a halogenated phenylquinazoline in a high boiling polar solvent in the presence of a catalytic mixture comprising a crown ether catalyst and a strong base, which yields a bis-quinazoline. The bis-quinazoline of this reaction is then thermally rearranged by heating it under an inert atmosphere to form a bis-quinazolinone which is subsequently hydrolyzed in an alcoholic solvent with a strong base to form the desired dianiline.

It is therefore a purpose of this invention to provide a synthesis process for preparing a dianiline from a bisphenol that is efficient and simple to perform.

A second purpose of this invention is to provide a synthetic method for preparing an intermediate compound for the synthesis of polymides containing electron-withdrawing substituents.

A further purpose of this process is to provide a method of providing diamines which are suitable for the use in the synthesis of polyimides which have high thermal resistance and good structural characteristics.

That we have accomplished these and other purposes will become obvious upon reference to the following detailed description of the invention.

DETAILED DESCRIPTION OF THE INVENTION

This invention is an inexpensive, high-yield process for synthesizing 2,2-bis-(aminophenyl)hexafluoropropane in an overall yield of 30% before optimization. The process is applicable to all phenols and bis-phenols having the formula

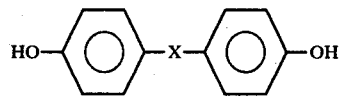

where X=a single bond, O, S, SO$_2$, CO, or C(CF$_n$H$_{3-n}$)$_2$ where n=0, 1, or 2.

Generally speaking a nucleophilic displacement reaction is utilized to convert an anhydrous bis-phenol to a bis-quinazoline from a halogenated phenylquinazoline whose structure is

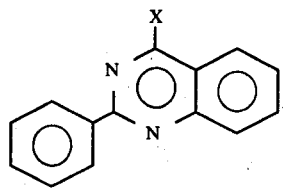

where X is chlorine, bromine or iodine. In order to insure a complete reaction between the principal reactants in an efficient manner, it is necessary to utilize a specific catalyst to increase the nucleophilicity of the hydroxy groups on the bis-phenol. In this connection, it has been discovered that the reaction will proceed in the presence of a crown ether catalyst and a strong base. Crown ether catalysts sold by Aldrich Chemical Co. of Milwaukee, Wis. under the trade names 18-Crown-6, dibenzo-18-Crown-6, dicyclohexano 18-Crown-6, and 15-Crown-5 are suitable for use in this process. These catalysts are mixed with strong bases such as sodium hydroxide and potassium hydroxide which are relatively inexpensive and commonly available. The nucleophilic displacement is conducted in the presence of a high-boiling, polar solvent such as dimethylsulfoxide (DMSO), dimethylacetamide (DMAC) or hexamethylphosphoramide (HMPA). The resulting bis-quinazoline is then placed in a pyrolytic reactor and heated in the presence of an inert atmosphere to form a bis-quinazolinone by a thermal rearrangement reaction. The bis-quiniazolinone is then placed in a reaction vessel provided with a condenser in the presence of an alcoholic solvent and a strong base, and refluxed to form the resulting diamine by hydrolysis.

A specific example of this process is shown below.

EXAMPLE

A benzene solution (100 ml) of 6.70 g (19.9 m moles) of Bisphenol-AF (obtained from DuPont, purified by sublimation) was treated with 42.0 ml of a 1.00 M potassium hydroxide (42.0 m moles) and the mixture was heated to distill off water azeotropically. After 3 hrs, the amount of water received in the Dean-Stark trap was quantitative.

The benzene solvent was removed by distillation under reduced pressure. Anhydrous dimethyl sulfoxide (DMSO) (100 ml) was added and the solution was treated with 10.8 g (45.0 m moles) of 4-chloro-2-phenylquinazoline (sold by Aldrich Chemicals Milwaukee, Wis., as AM-ex-OL ®) and 0.5 g of 18-Crown-6. The mixture was heated at 175°±5° C. for 24 hrs. After cooling, the mixture was filtered to yield 3.0 g of potassium chloride (40.3 mmoles, 100%). The filtrate was diluted with 1 liter of water and the precipitated solid was isolated by filteration and air dried thoroughly. An analytical sample was obtained by recrystallization from 1:1 dichloromethane-hexane, mp 179°–180° C. Yield: 9.70 g (13.0 mmoles 65.5%).

The product obtained above 9.70 g, 13.0 mmoles) was placed in a Schlenck tube purged with argon. The tube was immersed in a molten metal bath preheated to 315°–320° C. The solid melted to give a yellow oil. After heating at 320° C. for 15 hrs., the black oil was cooled and washed out of the tube with dichloromethane concentrating yielded a crystalline black solid which weighed 8.1 g (83.5%). Infrared analysis indicated the presence of the expected 1690 cm$^{-1}$ strong band for the bis-quiniazolinone product.

The crude material obtained above was mixed with 100 ml of ethylene glycol and 4 g of potassium hydroxide and then heated at reflux for 22 hrs. The mixture was cooled, diluted with 1 liter of water and extracted three times with 200 ml of dichloromethane. The organic extracts were combined and filtered through a bed of silica gel to give a light brown solution. Upon concentration and trituration of the residue with hexane, a grey-yellow powdery solid was obtained.

Infrared analysis showed the presence of an aromatic amine. The material was purified by column chromatography on silica gel, eluting with dichloromethane. Yield, 1.10 g (3.29 mmoles, 30.2%). The crystalline solid melted at 194°–195° C.

IR(KBr): 3464, 3374 (NH), 1631, 1521 (aromatic C=C), 1257, 1221, 1205, 1170 (CF$_3$), 965, and 829 cm$^{-1}$.

NMR (CDCl$_3$): δ4.30 (bs, 2H, N$\underline{H}_2$), 6.50, 6.65, 7.06, 7.25 ppm (distorted q, 4H, aromatic).

MS (70 ev): M$^+$ at 334.

Anal. Calc. for C$_{15}$H$_{12}$N$_2$F$_6$ (334.3): C, 53.90; H, 3.62; F, 34.10; N, 8.38. Found: C, 53.89; H, 3.71; F, 34.12; N, 8.29.

The process detailed in Example I is graphically summarized in the following reaction sequence. The optimization of times, temperature and resultants to increase the yield is within the skill of others skilled in the art based on the teachings provided herein. Therefore, the following process is not to to be construed as limited to these specific teachings.

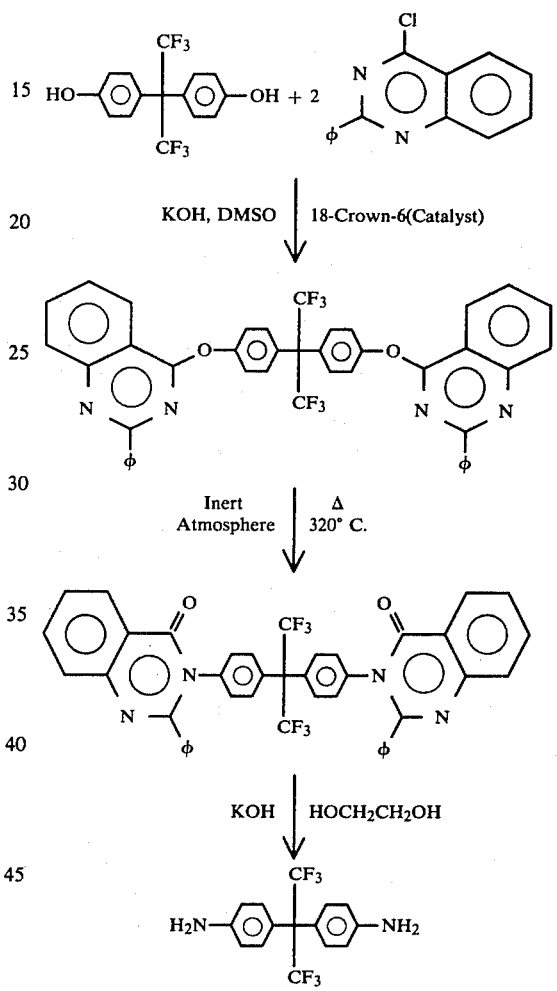

INDUSTRIAL APPLICABILITY

This invention is an inexpensive high-yield process for synthesizing anilines and dianilines from phenols and bisphenols. The process of this invention is simple and efficient and therefore it should have utility in the preparation of anilines and dianiline compounds for use in the synthesis of high-temperature, thermally stable polyimides and other structural resins.

Having completely disclosed the scope of my invention and providing teachings to enable others to make and use the same, the scope of my claims may now be understood as follows.

What is claimed is:

1. A process for conversion of bisphenols to dianilines comprising the steps of:
    a. forming the reaction product of an anhydrous bisphenol and a halogenated phenyl-quinazoline by heating said compounds in the presence of a crown ether catalyst, a strong base, and a high-boiling polar solvent;

b. subjecting said product to a thermal rearrangement by heating it in an inert atmosphere to thereby form a bis-quinazolinone; and c. hydrolyzing said bis-quinazolinone by refluxing it in the presence of a strong base in an alcoholic solvent, thereby forming a dianiline.

2. The process of claim 1 wherein said bis-phenol is a bis-phenol selected from the group whose formula is:

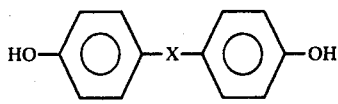

where X is a single bond, S, O, $SO_2$, CO, or $C(CF_nH_{3-n})$ where n is 0, 1 or 2.

3. A process in accordance with claim 1 wherein said halogenated phenylquinazoline is a compound whose structure is

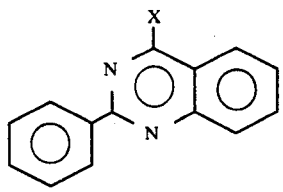

where X is Cl, Br or I.

4. The process of claim 1 or of claim 2 wherein said bis-phenol and said phenylquinazoline is heated in the presence of an 18-Crown-6 catalyst and potassium hydroxide.

5. The process of claim 2 wherein X in said bis-phenol contains a hexafluoroisopropylidene substituent.

6. An improved process for synthesizing 2,2-bis-(4-aminophenyl)hexafluoropropane comprising the steps of:

heating a solution of 2,2-bis(4-hydroxyphenyl)hexafluoropropane with 4-chloro-2-phenylquinazoline in the presence of a catalytic mixture formed from a crown ether catalyst and a strong base in a high-boiling polar solvent, thereby causing a nucleophilic displacement reaction to occur which yields a bisquinazoline;

heating said bis-quinazoline under an inert atmospheric purge thereby causing a thermal rearrangement to occur yielding a bisquinazolinone; and subsequently hydrolyzing said bisquinazoline by refluxing it in an alcoholic solvent with a strong base to form said bis(aminophenyl)hexafluoropropane which may be subsequently extracted from said alcoholic solvent and purified to a crystalline solid.

7. The process of claim 6 wherein said catalytic mixture is formed from an 18-Crown-6 catalyst and potassium hydroxide and wherein said polar solvent is dimethylsulfoxide.

8. The process of claim 6 wherein said bisquinazoline is heated at 320°±5° C. for at least 15 hours.

* * * * *